United States Patent [19]
Asano et al.

[11] Patent Number: 5,974,338
[45] Date of Patent: Oct. 26, 1999

[54] NON-INVASIVE BLOOD ANALYZER

[75] Inventors: Kaoru Asano, Kobe; Yasuhiro Kouchi, Kakogawa, both of Japan

[73] Assignee: Toa Medical Electronics Co., Ltd., Hyogo, Japan

[21] Appl. No.: 09/060,080

[22] Filed: Apr. 15, 1998

[30] Foreign Application Priority Data

Apr. 15, 1997 [JP] Japan ................................ 9-096274

[51] Int. Cl.$^6$ ........................................... A61B 5/00
[52] U.S. Cl. .......................................... 600/323; 600/322
[58] Field of Search ................................... 600/310, 322, 600/323, 326, 473, 476; 356/39, 41

[56] References Cited

U.S. PATENT DOCUMENTS

| | | |
|---|---|---|
| 4,998,533 | 3/1991 | Winkelman . |
| 5,372,136 | 12/1994 | Steuer et al. . |
| 5,598,842 | 2/1997 | Ishihara et al. . |
| 5,722,398 | 3/1998 | Ishihara et al. ................ 600/322 |

FOREIGN PATENT DOCUMENTS

| | | |
|---|---|---|
| 3-71135 | 11/1991 | Japan . |
| 7-308311 | 11/1995 | Japan . |
| 7-308312 | 11/1995 | Japan . |
| 8-299310 | 11/1996 | Japan . |
| 9-724066 | 7/1997 | WIPO . |

*Primary Examiner*—Eric F. Winakur

[57] ABSTRACT

A non-invasive blood analyzer includes a light source unit for irradiating a portion of a living body, the portion including a blood vessel, and includes an image capturing unit for capturing an image of the irradiated portion. An analyzing unit is included for setting an analysis region in the captured image and analyzing a blood vessel portion in the set analysis region. The image capturing unit captures images of the irradiated portion of the living body a plurality of times and the analyzing unit specifies analysis regions including the same blood vessel portions with respect to the captured images. The analyzing unit determines these regions based upon a position of a feature in sequential images and calculates at least one of blood vessel width, blood component concentration and blood component concentration ratio with respect to the blood vessel portion in each specified analysis region.

21 Claims, 12 Drawing Sheets

NON-INVASIVE BLOOD ANALYZER

CROSS-REFERENCE TO RELATED APPLICATIONS

This application is related to Japanese Patent Application No. HEI 09-096274 filed on Apr. 15, 1997 whose priority is claimed under 35 USC §119, the disclosure of which is incorporated herein by reference in its entirety.

BACKGROUND OF THE INVENTION

1. Field of the Invention

The present invention relates to a non-invasive blood analyzer and provides an apparatus for transcutaneously measuring a size of a blood vessel, a blood component concentration and a blood component concentration ratio in real time with excellent reproducibility without exsanguinating blood.

2. Description of the Related Arts

A method of directly measuring a blood vessel width by using images has been carried out with microcirculation (particularly at blood vessel on retina) as an object (refer to, for example, M. J. DEVANEY et al., "Continuous Measurement of Vascular Diameters via Television Microscopy", ISA TRANSACTION, Vol. 15, No. 1, pp. 73–78, 1976). However, according to the method, a blood vessel of several tens $\mu$m is measured as an object and accordingly, the method is not suitable for actual clinical use.

Further, an apparatus for measuring transcutaneously a hemoglobin concentration and a hematocrit has been devised. For example, there has been disclosed an apparatus of irradiating a plurality of wavelengths of light to a human body and measuring hemoglobin in blood from a change in an optical intensity caused by pulsation in "Hemoglobin concentration measuring apparatus" (Japanese Examined Patent Publication No. JP-B-3-71135). Similarly, there has been disclosed a method of calculating a hematocrit in blood by utilizing pulsation or the like in "System and method for non-invasive hematocrit monitoring" (U.S. Pat. No. 5,372,136).

However, these publications pose a problem in accurately calculating an absolute value, since an amount of blood for constituting an object of inspection is not specified. Further, it is anticipated that a difference is caused in measured value depending on a portion of the living body for mounting a sensor which is problematic in view of reproducibility or the like.

Further, although there has been disclosed a method of measuring the above-described items from images of red corpuscles flowing in a capillary in "Apparatus and method for in vivo analysis of RED and WHITE blood cell indices" (U.S. Pat. No. 4,998,533), according to the method, the system is extremely large-scaled.

Also, various non-invasive blood analyzers such as shown below are known. For example, an apparatus in which an image of an inside region of a blood vessel contained in a portion of a living body is captured to analyze the morphology and the number of blood cells from the obtained image (See U.S. Pat. No. 5,598,842 or Japanese Unexamined Patent Publication No. HEI 7(1995)-308312), an apparatus in which images of a blood vessel contained in a portion of a living body are captured by a plural number of times to determine a differential image thereof for detecting a blood cell image (See Japanese Unexamined Patent Publication No. HEI 7(1995)-308311), an apparatus provided with means for searching a blood vessel of a desired size contained in a portion of a living body by mechanically moving a transparent plate positioned in close contact with a skin surface of the living body so as to capture an image of the blood vessel through the transparent plate (See Japanese Unexamined Patent Publication No. HEI 8(1996)-299310), an apparatus in which an image of a blood vessel and a tissue contained in a portion of a living body is captured to calculate an amount of a blood component from an image density distribution distributed across the blood vessel in the captured image (See Published International Patent Application Number WO 97/24066) and the like are known.

Here, if images of a portion of a living body are to be captured time-sequentially by means of such a non-invasive blood analyzer to find a time-sequential change of an analysis value, an image capturing apparatus is separated from the living body after an image of the portion of the living body has been captured and, after several hours or several days, an image of the portion of the living body is captured again. However, since the reproducibility of the blood vessel portion whose images are to be captured is not ensured, it is difficult to obtain an analysis value accurately with respect to the same blood vessel portion.

SUMMARY OF THE INVENTION

The present invention has been carried out in consideration of the above-described situation and it is an object of the present invention to provide an apparatus capable of obtaining a time-sequential analysis value accurately with respect to the same blood vessel portion by specifying and analyzing analysis regions including the same blood vessel portions in a plurality of images captured time-sequentially, whereby it is possible to find changes occurring in response to various kinds of stimulus such as an exercise or a dialysis imposed upon a person to be inspected and effects produced in response to drug administration, and the like.

Accordingly, the present invention provides a non-invasive blood analyzer including a light source unit for irradiating a portion of a living body, the portion including a blood vessel; an image capturing unit for capturing an image of the irradiated portion; a holding member for holding the light source unit and the image capturing unit with respect to the portion of the living body; an analyzing unit for setting an analysis region in the captured image and analyzing a blood vessel portion in the set analysis region; and a displaying unit for displaying a result obtained by the analyzing unit, wherein the image capturing unit captures images of the irradiated portion of the living body a plural number of times and the analyzing unit specifies analysis regions including the same blood vessel portions with respect to the captured images and calculates at least one of a blood vessel width, a blood component concentration and a blood component concentration ratio with respect to the blood vessel portion in each specified analysis region.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
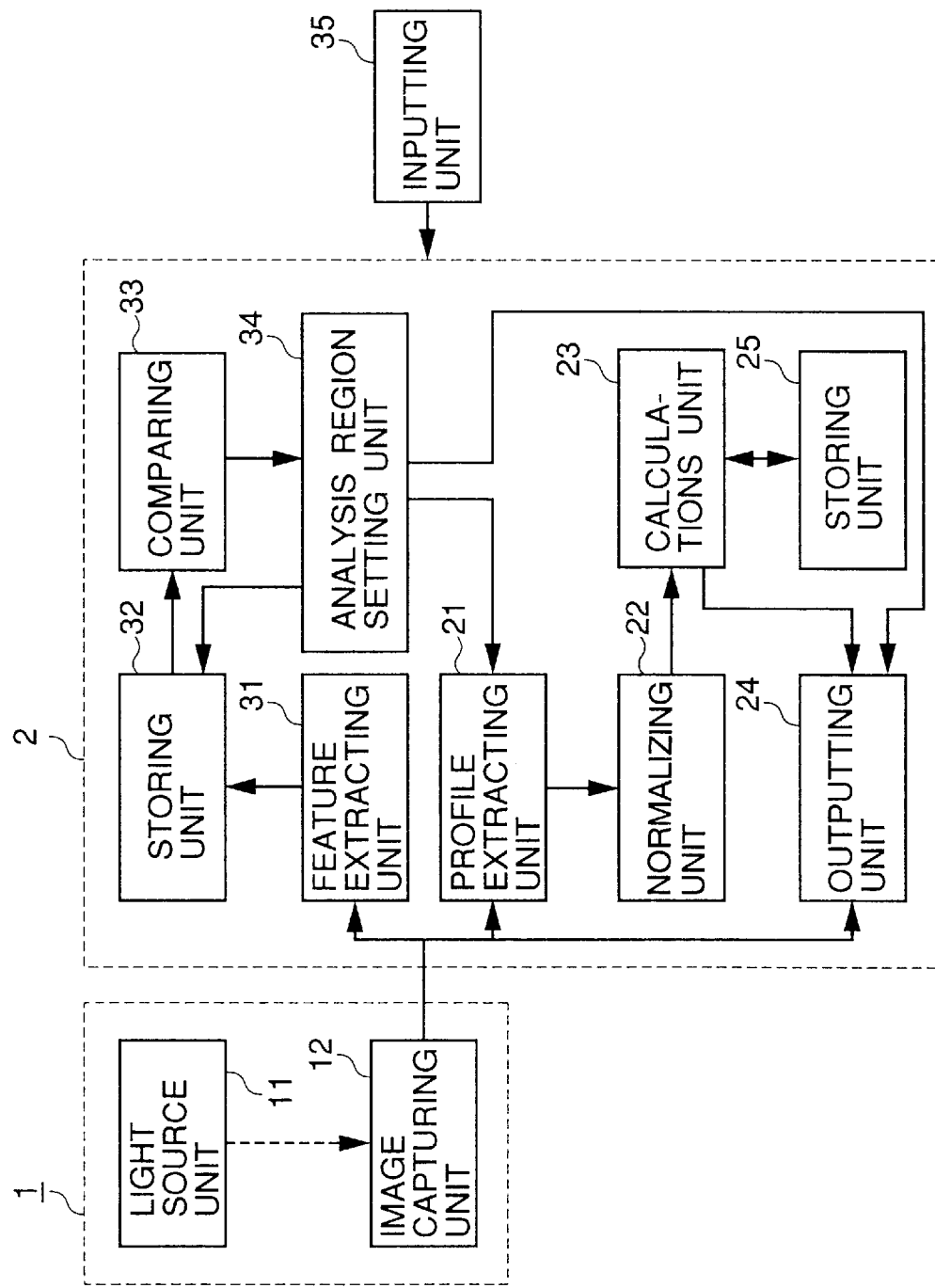
FIG. 1 is a block diagram showing a constitution of an embodiment according to the present invention.

In an apparatus according to the present invention, the living body designates a mammal including a human being and a portion of the living body designates not a tissue separated from a living body but a portion of a tissue of a living body as it is in which, for example, finger or earlobe or the like is pointed out.

The light source unit may employ a semiconductor laser (hereinafter, LD) or LED (Light Emitting Diode) or a halogen light source which may be irradiated to a portion of the living body directly or via a fiber. The wavelength of the light source is preferably within a range of 600 to 950 nm which can be transmitted through a tissue of a living body and where light absorption of water is inconsiderable.

The image capturing unit may be constituted by an optical system such as a lens or the like and an image capturing device such as a CCD (Charge Coupled Device) or the like.

Density distribution information of a blood vessel portion is provided at the image capturing unit. A line sensor or a photodiode array can be used as the image capturing device other than a CCD.

Further, the density distribution information can also be obtained by driving a single photodiode in a direction crossing a blood vessel.

Capturing images of the portion of the living body by a plural number of times may involve capturing images by a plural number of times with one wavelength or using a plurality of wavelengths to capture at least one image for each wavelength.

The optical system of the image capturing unit may be constituted simply by using only a lens for TV (for example, BD1214D made by COMICAR).

When the light source unit irradiates a portion of the living body, the image capturing unit can capture an image of the portion of the living body by receiving transmitted light or reflected light thereof.

Further, when the portion of the living body is a finger of a human hand, the holding member for holding the light source unit and the image capturing unit with respect to the portion of the living body may be a member for detachably fixing the finger between the light source unit and the image capturing unit. The holding member can employ a system of fitting the finger into a hole or groove in conformity with the shape of a finger or a system for pinching the finger from both sides using a pair of movable pieces.

In this case, although it is preferable to fix the finger at a position between the light source and the image capturing unit for excellent reproducibility, caution is required since when the finger is fixed by excessively strongly fastening or flexing it, a blood vessel is compressed with a congested state whereby a normal blood vessel image and measurement result cannot be obtained.

According to the present invention, the analyzing unit may comprise a feature extracting unit for extracting a morphological feature of the portion of the living body in each captured image, a feature storing unit for storing the extracted feature, a comparing unit for comparing the extracted features with each other, an analysis region setting unit for specifying regions including the same blood vessel portions in the images based on the compared features to set the specified region as the analysis region, and a calculating unit for calculating at least one of the blood vessel width, the blood component concentration and the blood component concentration ratio. An example of an analyzing unit may be a commercially available personal computer.

It is preferable that a morphological feature of a portion of the living body is based on at least one of a contour of a finger, a contour of a joint portion and an arrangement pattern of blood vessels.

The image capturing unit may capture images of the portion of the living body time-sequentially by a plural number of times; and the analyzing unit may permit the displaying unit to display a blood vessel width, a blood component concentration or a blood component concentration ratio provided by each of a plurality of images as a time-sequential change. The analyzing unit may permit the displaying unit to display the time-sequential change by a graph.

The blood component concentration according to the apparatus of the present invention, is, for example, a hemoglobin concentration or a hematocrit. In this case, it is preferable to use a wavelength (for example, 805 nm) or a wavelength band whereby light absorption by oxyhemoglobin and light absorption by deoxyhemoglobin are substantially equal to each other.

Further, it is preferable that the light source unit comprises at least one light emitting element selectively emitting light beams having first and second wavelengths or a plurality of light beams having wavelengths of three or more. For measuring a hemoglobin concentration or a hematocrit, it is preferable that each of the first and second wavelengths is a wavelength where light absorption by oxyhemoglobin and light absorption by deoxyhemoglobin are substantially equal to each other. The third wavelength may be a wavelength where light absorption by deoxyhemoglobin is sufficiently larger than light absorption by oxyhemoglobin. Thereby, an oxygenation ratio of hemoglobin (the ratio of oxyhemoglobin concentration with respect to the total hemoglobin concentration) can be measured.

Incidentally, although two wavelengths or more are needed in order to measure the hemoglobin concentration and the hematocrit or the oxygenation ratio, only one wavelength may be used to monitor the size of a blood vessel.

The light source unit may comprise a light source emitting a light beam having a wavelength where light absorption by oxyhemoglobin is substantially equal to light absorption by deoxyhemoglobin and the analyzing unit may calculate image density distribution at a portion crossing a blood vessel with respect to a captured image and calculate the blood vessel width based on the image density distribution.

The light source unit may comprise a light source emitting two light beams, each light beam having a respective wavelength where light absorption by oxyhemoglobin is substantially equal to light absorption by deoxyhemoglobin and the analyzing unit may calculate the image density distribution at a portion crossing a blood vessel in the analysis region of each image captured by using the light beams having the respective wavelengths and further calculate a hemoglobin concentration or a hematocrit based on the image density distributions.

The light source unit may comprise a light source emitting a light beam having a wavelength where light absorption by oxyhemoglobin is substantially equal to light absorption by deoxyhemoglobin and a light beam having another wavelength where the light absorption by deoxyhemoglobin is sufficiently larger than the light absorption by oxyhemoglobin and the analyzing unit may calculate the ratio of oxyhemoglobin concentration with respect to the concentration of total hemoglobin based on the image density distribution at the portion crossing the blood vessel in the analysis region of each image captured by using the light beams having the respective wavelengths.

According to the present invention, the concentration of a biochemical substance such as glucose, cholesterol, bilirubin or the like may be an object of analysis.

A detailed explanation will be given of the present invention based on embodiments shown by the drawings as follows. The present invention is not limited thereby.

FIG. 1 is a block diagram showing a constitution of a blood analyzer according to the present invention which can selectively execute a "blood vessel width measuring mode", a "blood component concentration measuring mode" and a "oxygenation ratio measuring mode". Referring to FIG. 1, a detecting unit 1 is provided with a light source unit 11 for irradiating a portion of the living body (human finger in this case) including a blood vessel and an image capturing unit 12 for capturing an optical image (image of transmitted light in this case) of an irradiated portion of the living body.

An analyzing unit 2 is provided with a feature extracting unit 31 for extracting a positional feature of a portion of the living body (coordinates of a recess in a contour at a position of a first joint of a finger in this case) in each image when the image capturing unit 12 captures an image of the portion of the living body a plural number of times, a storing unit 32 for storing the respective extracted features, a comparing unit 33 for comparing the respective features and an analysis region setting unit 34 for specifying an analysis region including the same blood vessel portion in each of the plurality of images based on a result of comparison.

Further, the analyzing unit 2 is provided with a profile extracting unit 21 for extracting an image density distribution at a portion linearly crossing orthogonally a blood vessel in the analysis region as an image density profile with respect to the captured image, a normalizing unit 22 for normalizing a morphological feature of the extracted density profile, a calculating unit 23 for calculating a diameter of a blood vessel, a blood component concentration, an oxygenation ratio and the like based on the normalized feature, a storing unit 25 for storing a result of calculation, and an outputting unit (CRT) 24 for outputting either the result of calculation or an image to a monitor. Incidentally, an inputting unit 35 comprises a keyboard and a mouse and carries out the setting of the measurement mode, the initial setting of the analysis region, the inputting of calculation conditions to the calculating unit 23 and so on. Further, the analyzing unit 2 is constituted by a personal computer.

Figure 2:
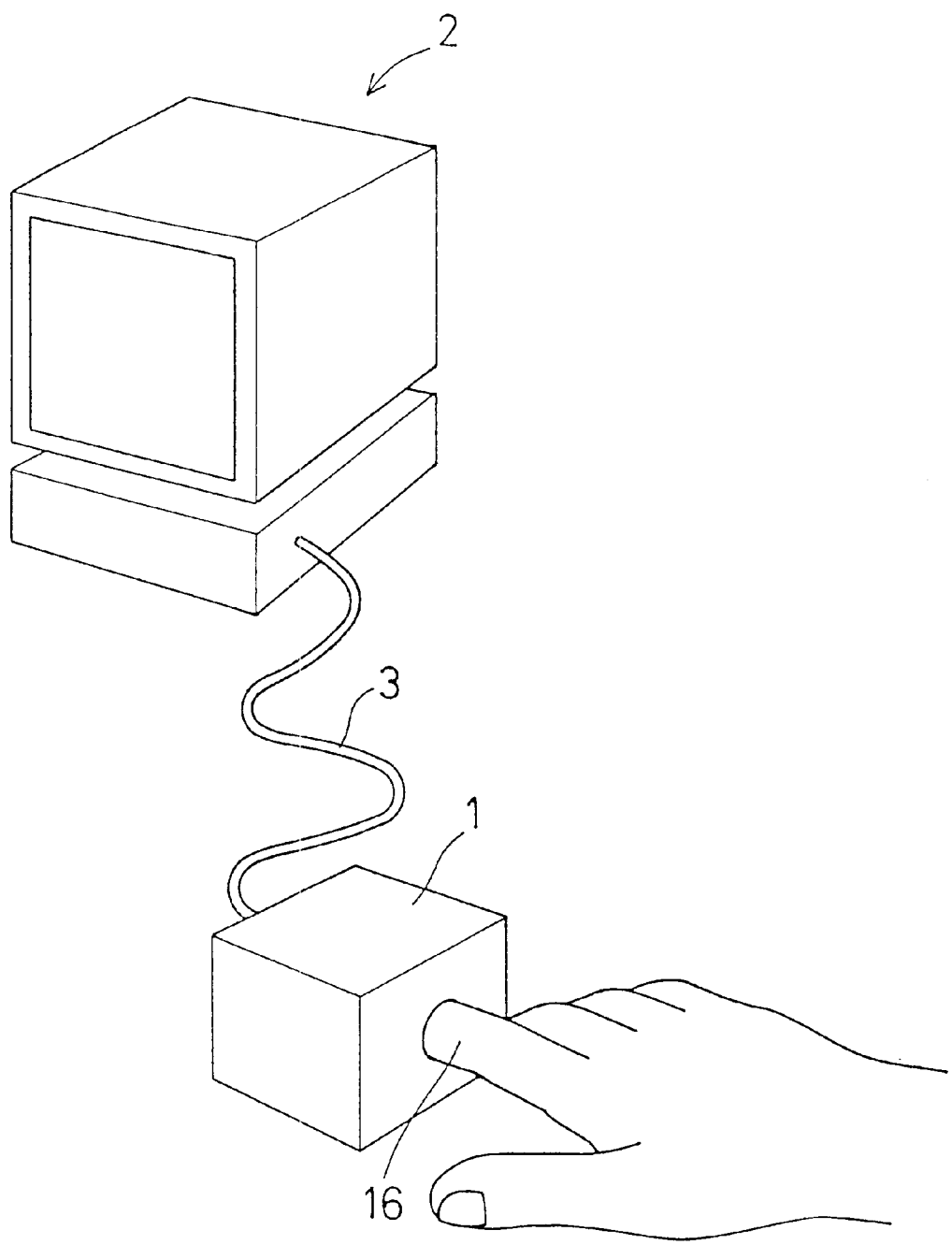
FIG. 2 is a perspective view showing an outer shape of the embodiment according to the present invention.
Figure 3:
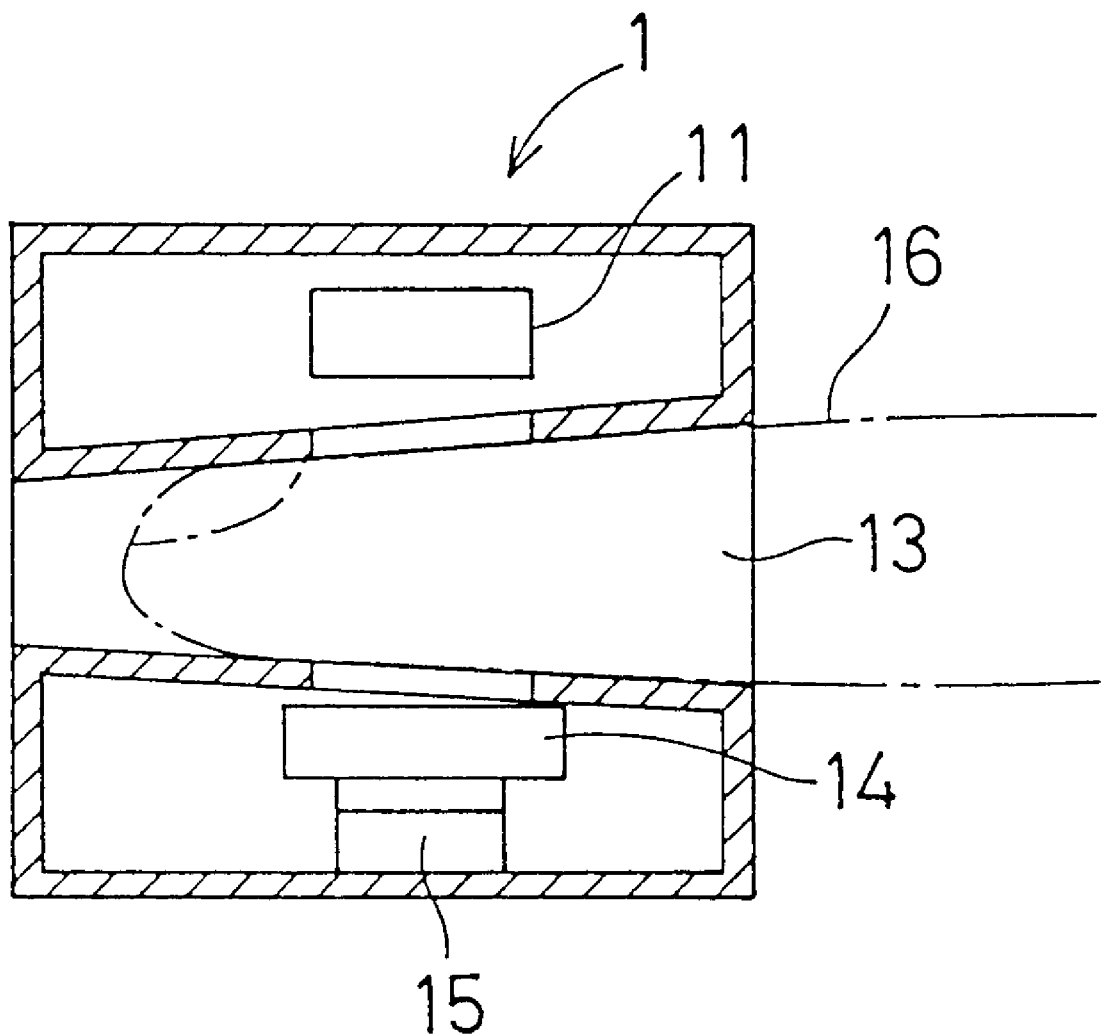
FIG. 3 is a sectional view showing an essential portion of the embodiment according the present invention.

FIG. 2 is a perspective view of outlook of the apparatus shown by FIG. 1 where the detecting unit 1 and the analyzing unit 2 are connected by a signal cable 3. FIG. 3 is a sectional view of the detecting unit 1 in which the detecting unit 1 is provided with the light source unit 11, the image capturing unit 12, that is, a lens 14 and an image capturing element 15. When a finger 16 is inserted into an opening portion 13, the light source unit 11 irradiates the finger 16 and an image produced by transmitted light is captured by the image capturing element 15 via the lens 14.

In this case, the opening portion 13 constitutes a holding member where the inner diameter is reduced toward the finger tip such that the inserted finger 16 can be fixed lightly.

Figure 11:
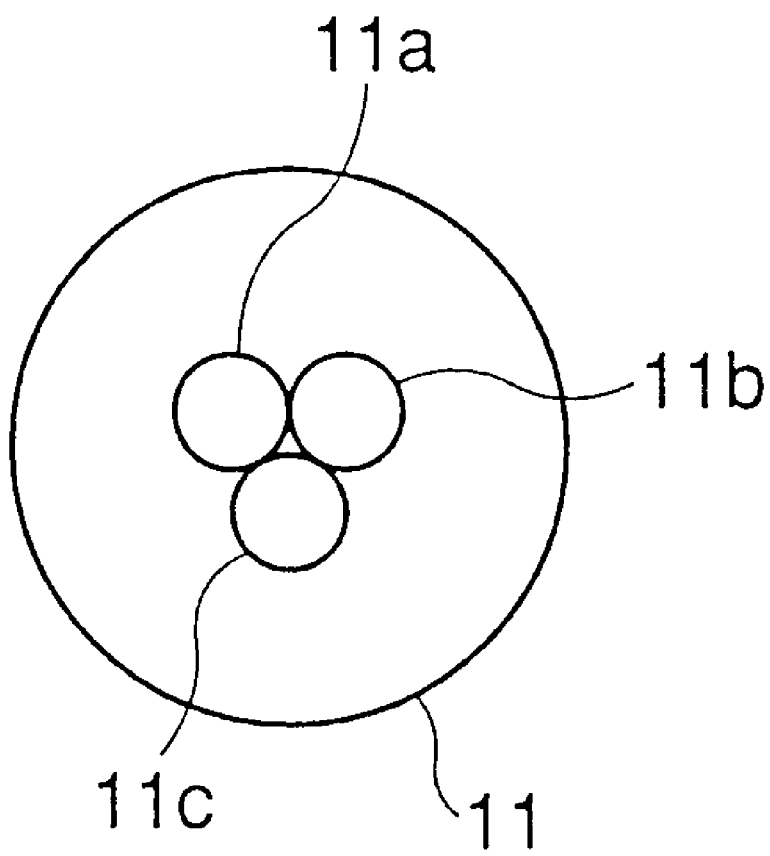
FIG. 11 is a front view of a light source in the embodiment according to the present invention.

Incidentally, the image capturing element 15 is a CCD. Further, FIG. 11 is a front view of the light source unit 11 where LED 11a, LED 11b and LED 11c are installed. According to the embodiment, each of the wavelengths (the first wavelength and the second wavelength) of LED 11a and LED 11b is selected so that the light absorption by oxyhemoglobin and the light absorption by deoxyhemoglobin are substantially equal to each other. The wavelength (the third wavelength) of LED 11c is selected so that the light absorption by deoxyhemoglobin is sufficiently larger than the light absorption by oxyhemoglobin.

That is, L3989 (made by Hamamatsu Photonix Co., Ltd.) having a central wavelength of 830 nm and a half value width of 40 nm is used as LED 11a; and L2656 (made by the same company) having a central wavelength of 890 nm and a half value width of 50 nm is used as LED 11b; and a LED (made by the same company) having a central wavelength of 660 nm and a half value width of 40 nm is used as LED 11c. Further, as mentioned later, only LED 11a is switched on in "blood vessel width measuring mode"; and LEDs 11a, 11b are switched on in "blood component concentration measuring mode"; and LEDs 11a, 11b, 11c are switched on in "oxygenation ratio measuring mode".

Figure 4:
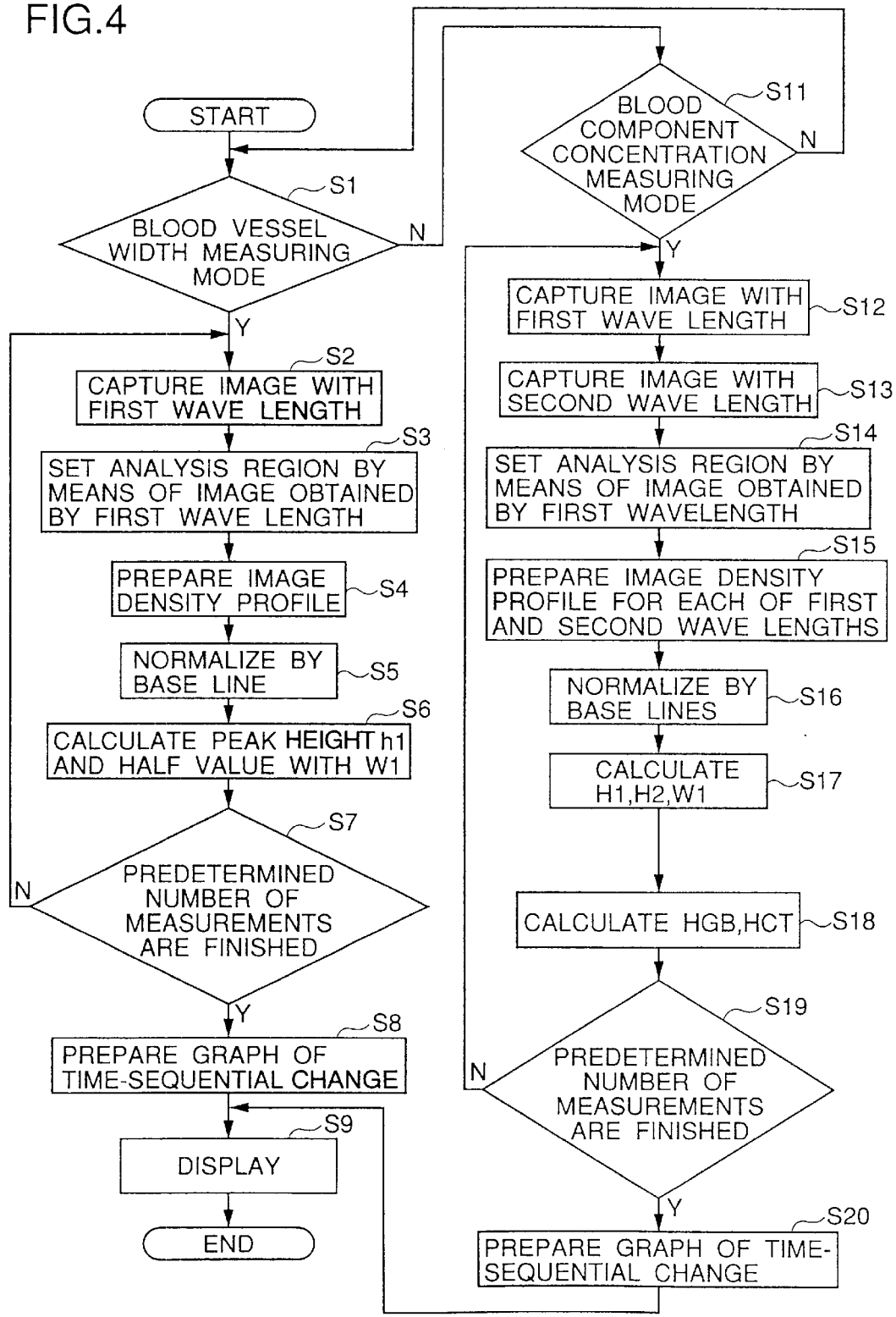
FIG. 4 is a flowchart showing an operation of the embodiment according the present invention.

The flow chart of FIG. 4 illustrates a procedure of measurement according to the present invention.

(1) Blood Vessel Width Measuring Mode

Figure 6:
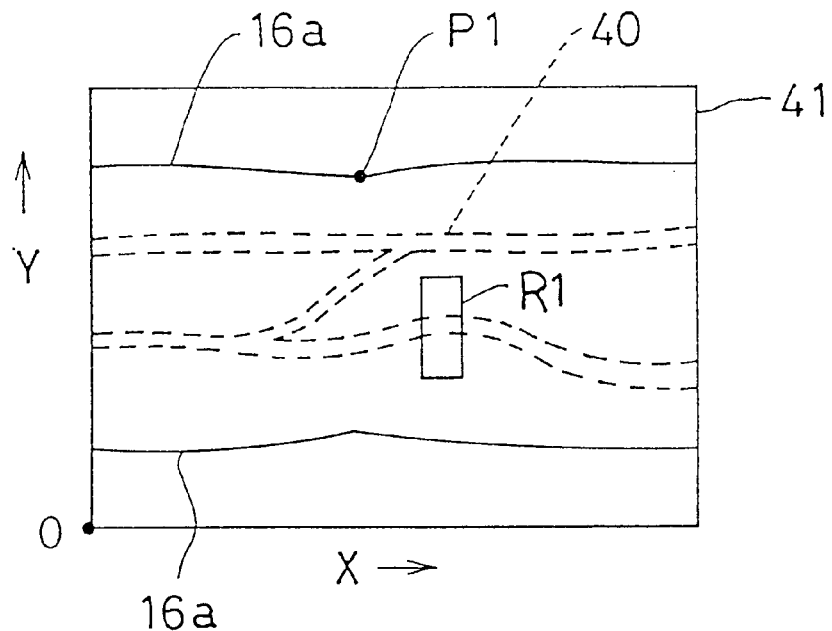
FIG. 6 is an explanatory view showing an example of an image provided by the embodiment according to the present invention.

In this mode, blood vessel images are captured time-sequentially a plural number of times by using one wavelength. First, "blood vessel width measuring mode" is set by operating the inputting unit 35 (step S1), as shown in FIG. 4. When the finger 16 is irradiated by LED 11a (first wavelength) and an image is captured, as shown by FIG. 6, an image 41 including a blood vessel (vein) image 40 locally present on the surface of the skin on the side of CCD 15 is obtained together with a contour 16a of the finger 16 (step S2). Next, an analysis region R1 is set in the image 41 (step S3).

Figure 5:
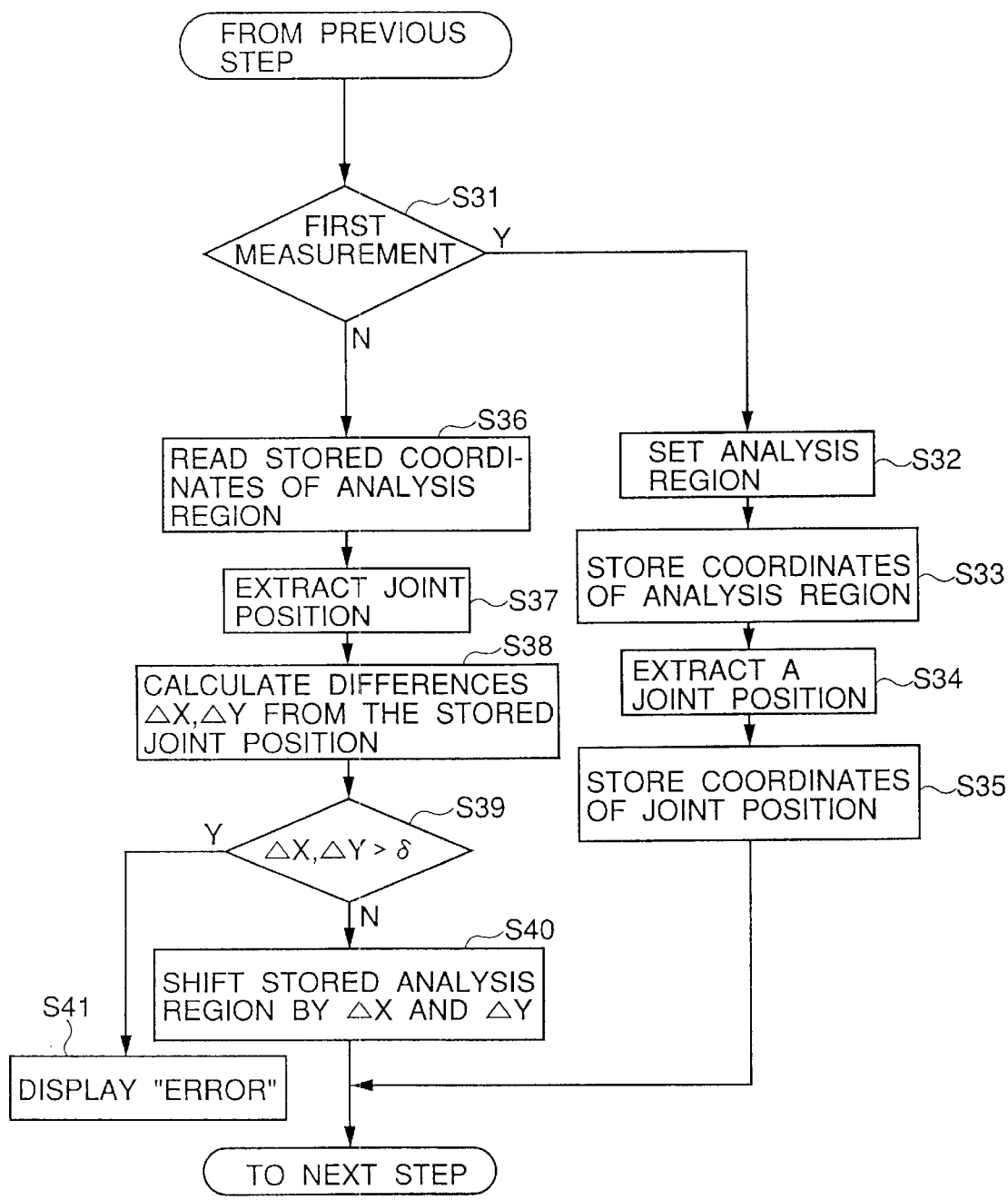
FIG. 5 is a flowchart showing another operation of the embodiment according to the present invention.

The procedure of setting the analysis region R1 is executed by a procedure shown by FIG. 5. That is, when the measurement is carried out for a first time (step S31), a region where the blood vessel image 40 has the best contrast is set as the analysis region R1 (step S32). Incidentally, although the analysis region R1 is automatically set by the analysis region setting unit 34, a user may set the analysis region R1 manually by operating the inputting unit 35 while observing an image of a monitor outputted to the outputting unit 24.

With respect to the set analysis region R1, coordinates of respective vertices of a quadrangle are stored in the storing unit 32 with a screen of the image 41 as an X-Y coordinates plane (step S33). Next, the feature extracting unit 31 extracts a joint position P1 from a recess of the contour 16a in the image 41 and allows the coordinates of the extracted position P1 to be stored into the storing unit 32 (steps S34, S35).

Figure 7:
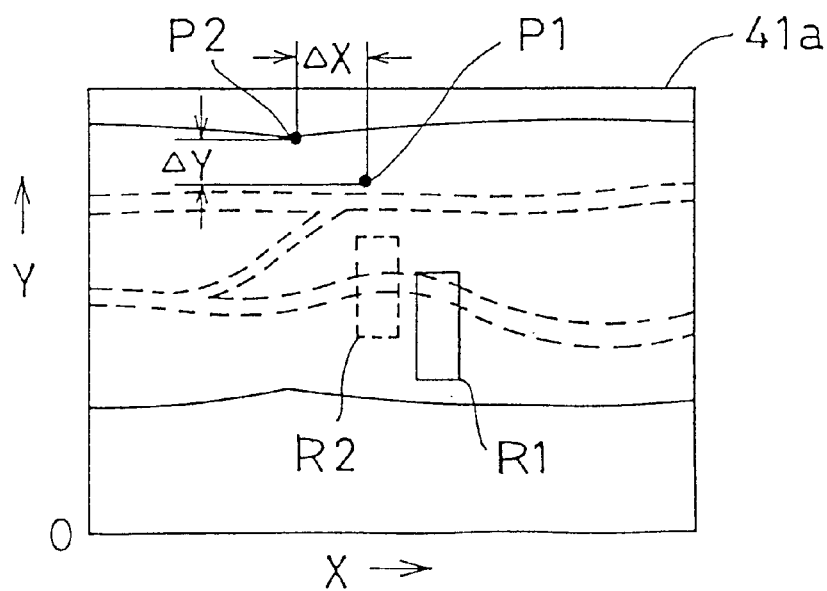
FIG. 7 is an explanatory view showing an example of an image provided by the embodiment according to the present invention.

Further, when the measurement is carried out at a second time or thereafter in step S31, in the case where, for example, an image 41a shown by FIG. 7 is provided in the previous step, the stored coordinates of the analysis region R1 are read and a joint position P2 is extracted from the image 41a by the feature extracting unit 31 (steps S36, S37).

Next, differences in coordinates ΔX and ΔY are calculated by the comparing unit 33 with respect to the joint position P1 which has been set in the measurement at the first time and the joint position P2 that is extracted at the current time (step S38). Further, when both of ΔX and ΔY are within a predetermined allowable range δ (step S39), the analysis region setting unit 34 sets a new analysis region R2 by shifting the initially set analysis region R1 by ΔX and ΔY (step S40).

Thereby, the blood vessel portion in the region R2 is substantially the same as the blood vessel portion in the region R1 which has been set in the measurement at the first time. In this way, even when "n" times of measurement is carried out with respect to a finger of a person to be inspected time-sequentially (for example, at intervals of 2 hours), the analysis regions R1, R2 . . . Rn are set at respective times and the measurement is carried out always with respect to the same portion of the blood vessel. Incidentally, when either of ΔX and ΔY exceeds the allowable value δ in step S39, the analyzing unit 2 judges that the finger 16 is not correctly placed with respect to the detecting unit 1, and "ERROR" is displayed in the outputting unit 24.

Figure 8:
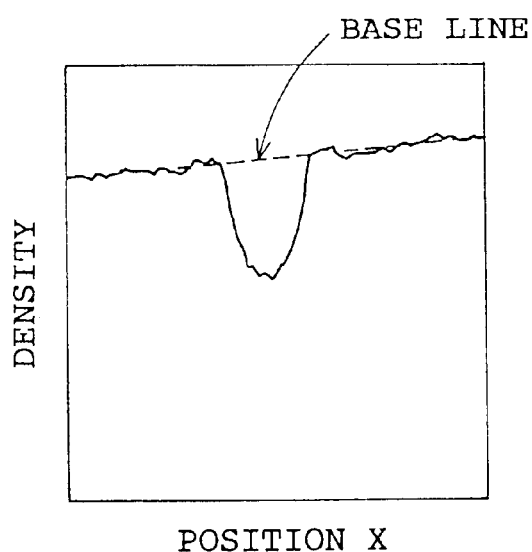
FIG. 8 is an explanatory view showing a density profile of an image in the embodiment according to the present invention.
Figure 9:
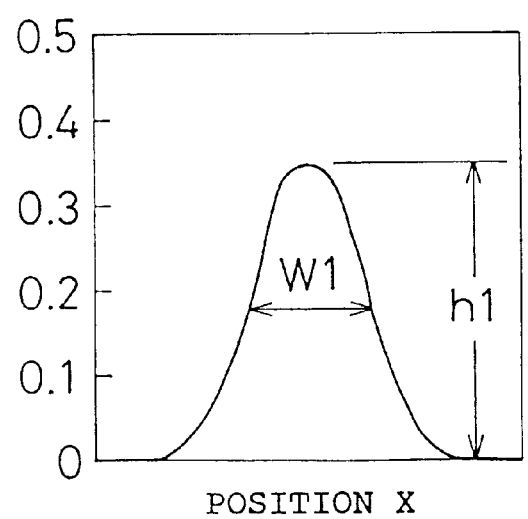
FIG. 9 is an explanatory view showing a normalized density profile in the embodiment according to the present invention.

Next, when the profile extracting unit 21 prepares a density profile (FIG. 8) in a direction orthogonal to the blood vessel in the set analysis region in step S4 of FIG. 4, the quantitating unit 22 normalizes the density profile by a base line. The base line is calculated by the least square method or the like from a density profile of a portion other than the blood vessel portion and the profile of FIG. 8 is normalized by the base line as shown by FIG. 9 (step S5). In this way, the density profile which is not dependent on an amount of incident light can be provided.

The calculating unit 23 calculates a peak height h1 from the normalized density profile (FIG. 9) and calculates a distribution width (half value width) w1 at (½)h1 as the blood vessel width and stores it in the storing unit 25 (step S6). Further, when a predetermined number of times of the measurement has been finished, a graph or a table representing a time-sequential change of the calculated blood vessel width is prepared and displayed (steps S7 through S9).

Figure 12:
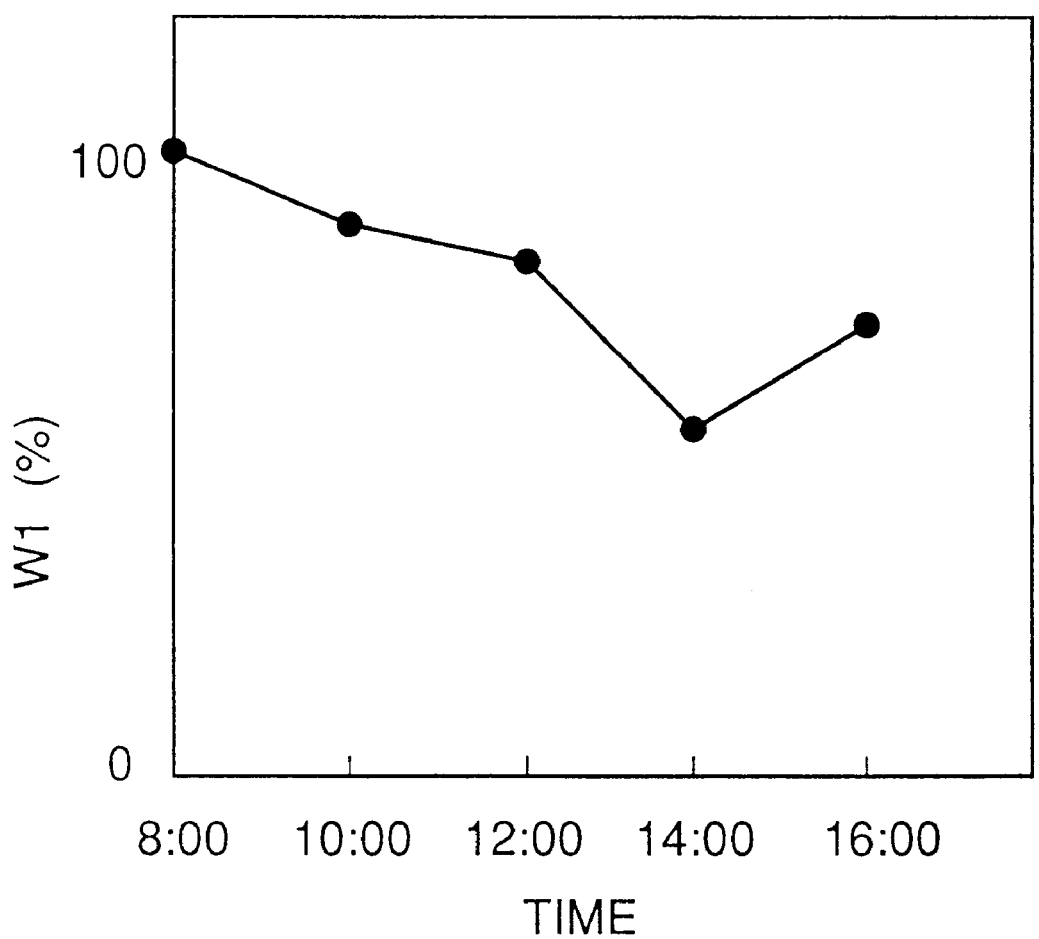
FIG. 12 is an explanatory view showing a display example in the embodiment according to the present invention.

FIG. 12 shows an example of displaying a relative time-sequential change of the blood vessel width w1 in a graph by the outputting unit 24 when the measurement is carried out at intervals of 2 hours with respect to a finger of a person to be inspected.

This shows the amount of time-sequential change in the blood vessel width w1. Also, it is possible to find the behavior of the blood vessel width in response to an exercise, dialysis, or various kinds of stimulus, which is clinically useful.

(2) Blood Component Concentration Measuring Mode

In this mode, an operation of capturing one image for each of the two wavelengths is carried out time-sequentially by a plural number of times. First, "blood component concentration measuring mode" is set by operating the inputting unit 35 (step S11), as shown in FIG. 4. The finger 16 is irradiated successively by LED 11a (first wavelength) and LED 11b (second wavelength) and images are respectively captured (steps S12, S13). An analysis region is set with respect of the image captured by the first wavelength by a procedure the same as that in step S3, that is, the procedure shown by FIG. 5 (step S14).

Figure 10:
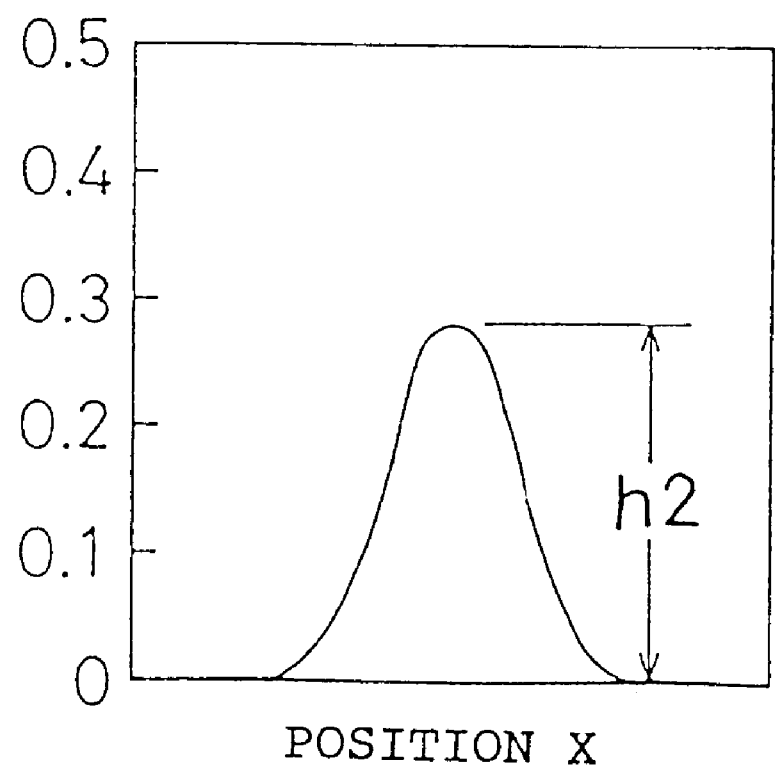
FIG. 10 is an explanatory view showing another normalized density profile in the embodiment according to the present invention.

Next, the profile extracting unit 21 prepares a first density profile and a second density profile as shown in FIG. 8 for the images obtained by the first wavelength and the second wavelength, respectively (step S15). The quantitating unit 22 normalizes the first and second density profiles by base lines as shown in FIG. 9 and FIG. 10, respectively (step S16). Then, the calculating unit 23 calculates a peak height h1 and a half value width w1 of the normalized first density profile (FIG. 9) and calculates a peak height h2 of the normalized second density profile (FIG. 10) in a similar manner (step S17), and calculates a hemoglobin concentration (HGB) and a hematocrit (HCT) in the following way (step S18).

That is, when the scattering coefficient of blood at a first wavelength is designated by notation S1 and the light absorption coefficient thereof is designated by notation A1, Beer's Law is established approximately, $$\log(1-h1) = -k(S1+A1)w1 \qquad (1)$$

where notation k designates a proportional constant.

Meanwhile, the scattering coefficient S1 and the light absorption coefficient A1 seem to be proportional respectively to the hematocrit HCT and the hemoglobin amount of blood. Therefore, $$S1 = \sigma1 \cdot HCT, \quad A1 = \epsilon1 \cdot HGB \qquad (2)$$

where notations σ1 and ε1 designate proportional constants. Accordingly, $$\log(1-h1) = -(k\sigma1 \cdot HCT + k\epsilon1 \cdot HGB) \cdot w1 \qquad (3).$$

Then, also with respect to the peak height h2 obtained from the image by LED 11b (second wavelength) the following relationship is established where $S2 = \sigma2 \cdot HCT$ and $A2 = \epsilon2\epsilon HGB$ (notations σ2 and ε2 designating proportional constants).

$$Log(1-h2) = -k(S2+A2) \cdot w1 \quad (4)$$
$$= -(k\sigma 2 \cdot HCT + k\varepsilon 2 \cdot HGB) \cdot w1$$

k, σ1, σ2, ε1 and ε2 are theoretically or experimentally determined and accordingly, when h1, h2 and w1 are obtained, HGB and HCT are calculated by equations (3) and (4).

Meanwhile, the image is actually dimmed by a tissue present from the blood vessel to the epiderm and accordingly, the observed peak value is reduced compared with that in the case where the tissue is not present. Accordingly, the equation that practically holds is:

$$\log(1-h1) = -k(S+A)w1 + T \quad (5)$$

where notation S designates the scattering coefficient of blood, notation A designates the light absorption coefficient of blood and notation T designates a term representing influence by living body tissue.

Now, it has been experimentally found that T is made to be comparatively constant by selecting, as the analysis region, a portion among the obtained images where the contrast of the blood vessel image is maximized. Accordingly, if an experimentally obtained T is used, there poses no particular problem in determining HGB and HCT.

Calculated HGB and HCT are stored into the storing unit 25. When such a measurement is repeated by a predetermined number of times, the calculating unit 23 prepares a graph or a table representing a time-sequential change of the calculated values and displays it (steps S19, S20).

Figure 13:
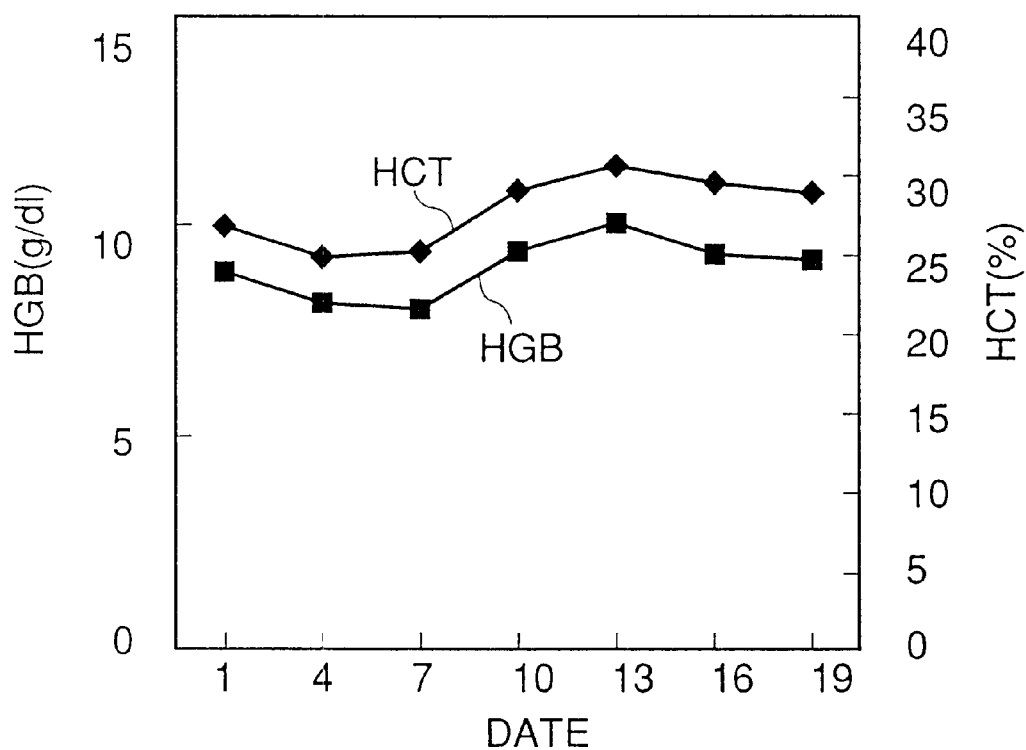
FIG. 13 is an explanatory view showing another display example in the embodiment according to the present invention.

FIG. 13 shows an example in which the measurement has been carried out at intervals of 2 days with respect to a finger of a person to be inspected and time-sequential changes of HGB and HCT are displayed by the outputting unit 24 in graphs. This shows the presence or absence of bleeding, the effects provided by alimentotherapy or drug administration and the like, which are clinically useful.

(3) Oxygenation Ratio Measuring Mode

In this mode, an operation of capturing an image for each of the plurality of wavelengths is carried out (time-sequentially) for a plural number of times.

Figure 14:
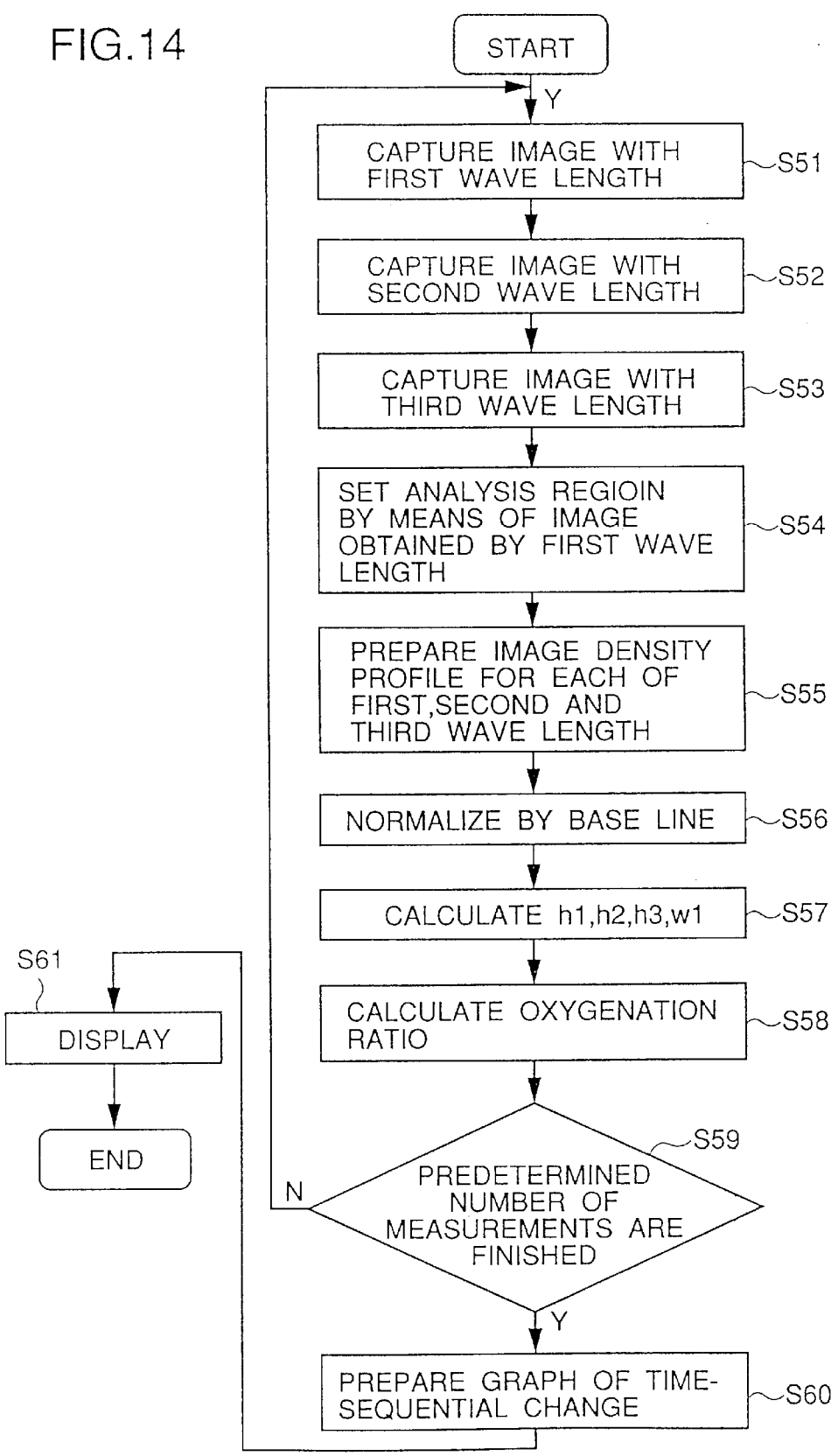
FIG. 14 is a flowchart showing still another operation of the embodiment according to the present invention.

First, "oxygenation ratio measuring mode" is set by the inputting unit 35. Then, the finger 16 is irradiated by LED 11a (first wavelength: 830 nm) as shown in FIG. 14 and an image is captured (step S51). Next, the finger 16 is irradiated by LED 11b (second wavelength: 890 nm) and an image is captured similarly (step S52). Then, the finger 16 is irradiated by LED 11c (third wavelength: 660 nm) and an image is captured similarly (step S53). Further, the analysis region is set by taking a procedure shown in FIG. 5 (step S54).

Next, a density profile of the image for each of the first, second and third wavelengths is prepared as shown in FIG. 8 (step S55). Then, each density profile is normalized (step S56), and the peak heights h1, h2, h3 and the width w1 are calculated (step S57).

Next, the oxygenation ratio is calculated and stored into the storing unit 25 (step S58). The measurement may be repeated for a predetermined number of times to prepare and display a graph or a table representing the time-sequential change (steps S59 through S61).

Here, an explanation will be given of the principle of calculating the oxygenation ratio in step S58.

That is, when the total amount of hemoglobin is designated by notation HGB, the amount of oxyhemoglobin is designated by notation HGBo, and the amount of deoxyhemoglobin is designated by HGBr, then the following equation holds:

$$HGB = HGBo + HGBr \quad (6)$$

Also, the light absorption of oxyhemoglobin and deoxyhemoglobin with respect to the first wavelength is designated by ε1 (since the light absorptions by these are equal to each other), the light absorption of oxyhemoglobin and deoxyhemoglobin with respect to the second wavelength is designated by ε2 (since the light absorptions by these are equal to each other), and the light absorptions of oxyhemoglobin and deoxyhemoglobin with respect to the third wavelength are designated by ε3o and ε3r, respectively.

Further, the light absorption coefficient of blood at a first wavelength is designated by notation A1 and the scattering coefficient thereof is designated by notation S1; the light absorption coefficient of blood at a second wavelength is designated by notation A2 and the scattering coefficient thereof is designated by notation S2; and the light absorption coefficient of blood at a third wavelength is designated by notation A3 and the scattering coefficient thereof is designated by notation S3; the peak heights of the normalized density profiles with respect to the three wavelengths are designated by notations h1, h2, h3, respectively; and the width is designated by notation w1. Then, the following equations hold in the same manner as the equation (1).

$$\log(1-h1) = -k(A1+S1)w1 \quad (7)$$
$$\log(1-h2) = -k(A2+S2)w1 \quad (8)$$
$$\log(1-h3) = -k(A3+S3)w1 \quad (9)$$

From the equations (7) and (8), the coefficients A1, A2, S1, S2 are determined.

Meanwhile, the scattering coefficient S3 seems to be proportional to the hematocrit HCT of blood in the same manner as the scattering coefficients S1, S2, so that the following equation holds:

$$S3 = \sigma 3 \cdot HCT \quad (10)$$

Therefore, the light absorption coefficient A3 is determined from the equations (9) and (10).

Here, from the definitions of the light absorption coefficients A1 and A3, $$A3/A1 = (\varepsilon 3o \cdot HGBo + \varepsilon 3r \cdot HGBr)/(\varepsilon 1 \cdot HGB) \quad (11)$$

Since ε3r >> ε3o, $$A3/A1 = (\varepsilon 3r \cdot HGBr)/(\varepsilon 1 \cdot HGB) \quad (12)$$
$$= a \cdot HGBr/HGB$$

where a = ε3r/ε1.

From the definition of the oxygenation ratio, $$r = HGBo/HGB \quad (13)$$
$$= 1 - HGBr/HGB = 1 - (1/a) \cdot (A3/A1)$$

whereby the oxygenation ratio is calculated.

Here, it is to be noted that the clinical significance of oxygenation ratio of the vein is, at present, not as definite as the significance of oxygen saturation of artery blood. However, it seems that the oxygen saturation of the vein reflects the amount of spare oxygen in the living body, because the difference between the oxygen saturation of the artery and the oxygen saturation of the vein is the amount of oxygen which is actually consumed. With this invention as a turning point, it is expected that the clinical significance of the oxygenation ratio will be recognized.

According to the present invention, the blood vessel width, the blood component concentration, the blood component concentration ratio and the like can be measured with few dispersion factors, since the same blood vessel portion is analyzed with respect to the obtained plural images. Also, by capturing an image of a portion of the living body time-sequentially in a plural number of times, even a detailed time-sequential change in the state of the person to be inspected can be observed from the images. Further, by extracting and comparing the features of a portion of the living body using the captured images, the same blood vessel portion can be specified without the need for separately providing a special mechanism.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A non-invasive blood analyzer comprising:
   image capturing means for capturing an image of a portion of a living body irradiated by light, the portion including a blood vessel; and
   analyzing means for extracting a position of a feature within a captured image of the living body to determine a specified analysis region,
   wherein the image capturing means sequentially captures images of the irradiated portion of the living body a plurality of times, and the analyzing means compares an extracted position of the feature within a first captured image to an extracted position of the feature within a sequentially captured image to determine the specified analysis region, and calculates blood information from a blood vessel in the specified analysis region.

2. The non-invasive analyzer according to claim 1, further comprising a display unit, wherein the image capturing means captures images of the portion of the living body time-sequentially a plurality of times, and wherein results of calculations obtained from the captured images are displayable as a time-sequential change on the displaying unit.

3. The non-invasive blood analyzer according to claim 1, further comprising a light source for emitting a light beam having a wavelength where light absorption by oxyhemoglobin is substantially equal to light absorption by deoxyhemoglobin wherein the analyzing means calculates an image density distribution at a portion crossing the blood vessel with respect to each of the captured images and calculates blood vessel width based on the image density distribution.

4. The non-invasive blood analyzer according to claim 1, further comprising a light source for emitting two light beams, each light beam having a respective wavelength where light absorption by oxyhemoglobin is substantially equal to light absorption by deoxyhemoglobin, wherein the analyzing means calculates an image density distribution at a portion crossing the blood vessel in the analysis region of each of the images captured by using the light beams having the respective wavelengths and calculates a hemoglobin concentration or a hematocrit based on the image density distributions.

5. The non-invasive blood analyzer according to claim 1, further comprising a light source for emitting a light beam having a wavelength where light absorption by oxyhemoglobin is substantially equal to light absorption by deoxyhemoglobin and, a light beam having another wavelength where the light absorption by deoxyhemoglobin is sufficiently larger than the light absorption by oxyhemoglobin, wherein the analyzing means calculates a ratio of oxyhemoglobin concentration with respect to a concentration of total hemoglobin based on an image density distribution at a portion crossing the blood vessel in the analysis region of each image captured by using the light beams having the respective wavelengths.

6. The non-invasive analyzer according to claim 1, wherein the blood information calculated is one of a blood vessel width, a blood component concentration and a blood component concentration ratio.

7. The non-invasive analyzer according to claim 1, wherein the portion of the living body is a human finger and the feature of the living body is based on one of a contour of the finger, a contour of a joint portion and an arrangement pattern of blood vessels.

8. An analyzing unit for a non-invasive blood analyzer, comprising:
   capturing means for sequentially capturing an image of an irradiated portion of a living body, including a blood vessel, a plurality of times;
   extracting means for extracting morphological features of the living body from each of the sequentially captured images;
   storing means for storing the extracted features;
   comparing means for comparing the extracted features with each other;
   analyzing means for specifying an analysis region based on the compared; and
   calculating means for calculating blood information from a blood vessel in the specified analysis region.

9. The non-invasive blood analyzer according to claim 8, wherein the portion of the living body is a human finger and the feature of the living body is based on at least one of a contour of the finger, a contour of a joint portion and an arrangement pattern of blood vessels.

10. The analyzing unit according to claim 8, wherein the blood information calculated is one of a blood vessel width, a blood component concentration and a blood component concentration ratio.

11. A non-invasive blood analyzing method comprising the steps of:
    irradiating a portion of the living body, the portion including a blood vessel;
    capturing sequential images of the irradiated portion of the living body a plurality of times;
    extracting morphological features of the portion of the living body from each of the sequentially captured images;
    comparing the extracted features with each other;
    specifying regions including the same blood vessel portions in the sequentially captured images based on the compared features; and
    calculating at least one of blood vessel width, blood component concentration and blood component concentration ratio with respect to each specified analysis region.

12. A method of analyzing blood information, comprising the steps of:
    capturing a first image of an irradiated portion of a living body;
    setting an initial analysis region based on the first captured image;

determining a first position of a feature within the first captured image;

capturing a sequential image of said irradiated portion of the living body;

determining a second position of the feature within the sequentially captured image;

comparing the second position with the first position;

shifting the initial analysis region to a new analysis region, wherein the amount shifted is within a predetermined range based on the compared positions; and analyzing blood information within the new analysis region.

13. A method according to claim 12, wherein the step of determining a first position further comprises extracting a first position of a joint and storing coordinates of the first position of the joint.

14. A method according to claim 13, wherein the step of determining a second position further comprises extracting coordinates of a second position of the joint.

15. A method according to claim 14, wherein the step of comparing further comprises calculating horizontal and vertical position differences between coordinates of the first position and the second position of the joint.

16. A method according to claim 15, wherein the step of calculating differences further comprises comparing horizontal and vertical position differences within a predetermined tolerance.

17. A method according to claim 16, further comprising the step of generating an error signal if the horizontal and vertical position differences are greater than said predetermined tolerance.

18. A non-invasive blood analyzer comprising:

image capturing means for capturing an image of a portion of a living body irradiated by light, the portion including a blood vessel; and analyzing means for analyzing the captured image, wherein the image capturing means sequentially captures images of the irradiated portion of the living body a plurality of times, the analyzing means extracting features from the captured images, comparing the extracted features, specifying analysis regions including the same blood vessel portions in the captured images based on the comparison and calculating blood information values from the same portions in the captured images.

19. A non-invasive blood analyzer comprising:

image capturing means for capturing an image of a portion of a living body irradiated by light, the portion including a blood vessel;

analyzing means for analyzing the captured image; and a display unit to display an analyzed result, wherein the image capturing means sequentially captures images of the irradiated portion of the living body a plurality of times, the analyzing means calculating blood information values from the same blood vessel portions in the captured images, the display unit displaying the calculated blood information values in time series on a time coordinated system.

20. A non-invasive blood analyzer comprising:

a light source for irradiating a portion of a living body, the portion including a blood vessel;

image capturing means for capturing images of the irradiated portion of the living body, and analyzing means for calculating blood information values from the same blood vessel portions in the captured images, wherein the light source selectively emits first and second light beams, the first light beam having a wavelength where light absorption by oxyhemoglobin is substantially equal to light absorption by deoxyhemoglobin, the second light beam having a wavelength where the light absorption by deoxyhemoglobin is sufficiently larger than the light absorption by oxyhemoglobin, the image capturing means captures a set of images under the first and second light beams respectively, and the analyzing means specifies analysis regions including the same blood vessel portions in the set of images and calculates a ratio of oxyhemoglobin concentration with respect to a concentration of total hemoglobin based on an image density distribution at a portion crossing the same blood vessel in each image.

21. A non-invasive blood analyzer comprising:

a light source for irradiating a portion of a living body, the portion including a blood vessel;

image capturing means for capturing images of the irradiated portion of the living body, and analyzing means for calculating blood information values from the same blood vessel portions in the captured images, wherein the light source selectively emits first, second and third light beams, each of the first and second light beams having a respective wavelength where light absorption by oxyhemoglobin is substantially equal to light absorption by deoxyhemoglobin, the third light beam having a wavelength where the light absorption by deoxyhemoglobin is sufficiently larger than the light absorption by oxyhemoglobin, the image capturing means captures a set of images under the first, second and third light beams respectively, and the analyzing means specifies analysis regions including the same blood vessel portions in the set of images and calculates a hemoglobin concentration or a hematocrit based on an image density distribution at a portion crossing the same blood vessel in each of the images captured under the first and second beams, and a ratio of oxyhemoglobin concentration with respect to a concentration of total hemoglobin based on a image density distribution at a portion crossing the same blood vessel in each of the images captured under the first and third beams.

* * * * *